United States Patent [19]

Moeller et al.

[11] Patent Number: 4,705,682
[45] Date of Patent: Nov. 10, 1987

[54] OLIGOPEPTIDE DERIVATIVES, THEIR PRODUCTION AND THEIR USE AS SURFACTANTS GENTLE TO THE SKIN

[75] Inventors: Hinrich Moeller, Monheim; Ulrich Zeidler, Duesseldorf, both of Fed. Rep. of Germany

[73] Assignee: Henkel Kommanditgesellschaft auf Aktien, Duesseldorf, Fed. Rep. of Germany

[21] Appl. No.: 860,143

[22] Filed: May 6, 1986

[30] Foreign Application Priority Data

May 13, 1985 [DE] Fed. Rep. of Germany ....... 3517205

[51] Int. Cl.$^4$ .......................... C07K 1/12; C08H 1/06
[52] U.S. Cl. ..................... 424/70; 252/356; 252/DIG. 5; 530/343; 530/354; 530/356; 530/377; 530/378; 530/407
[58] Field of Search ............. 530/354, 356, 377, 378, 530/407, 343; 424/70; 252/356

[56] References Cited

U.S. PATENT DOCUMENTS

| | | | |
|---|---|---|---|
| 2,411,215 | 11/1946 | Kise et al. | 260/342.4 |
| 2,525,753 | 10/1950 | Yutzy et al. | 530/354 |
| 2,827,419 | 3/1958 | Tourtellotte et al. | 530/354 X |
| 3,108,995 | 10/1963 | Tourtellotte et al. | 530/354 |
| 3,138,581 | 6/1964 | Young et al. | 260/112 |
| 3,764,711 | 10/1973 | Melnychyn et al. | 530/377 X |
| 3,824,228 | 7/1974 | Eckert et al. | 530/345 X |
| 4,115,548 | 9/1978 | Marsh et al. | 424/70 |
| 4,140,759 | 2/1979 | Mausner | 424/70 |
| 4,195,077 | 3/1980 | Marsh et al. | 530/378 X |
| 4,234,475 | 11/1980 | Sokol | 530/354 X |
| 4,338,214 | 7/1982 | Fischer et al. | 252/545 |
| 4,406,833 | 9/1983 | Boehme et al. | 530/407 X |
| 4,451,385 | 5/1984 | Tavss et al. | 530/417 X |

FOREIGN PATENT DOCUMENTS

| | | |
|---|---|---|
| 28779 | 5/1981 | European Pat. Off. . |
| 50686 | 5/1982 | European Pat. Off. . |
| 1959651 | 11/1973 | Fed. Rep. of Germany . |

OTHER PUBLICATIONS

Chemical Abstracts 92:203420j, S. Tani, Toilet Article Composition, Jun., 1980.
Chemical Abstracts 93:53793n, T. Miyata, Cosmetic Compositions Containing Collagen Derivatives, Aug., 1980.
"Methoden der Organischen Chemie," vol. IX/2, (1958), pp. 297–298.

*Primary Examiner*—Howard E. Schain
*Attorney, Agent, or Firm*—Ernest G. Szoke; Henry E. Millson, Jr.; Mark A. Greenfield

[57] ABSTRACT

Oligopeptide derivates corresponding to the general formula

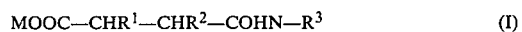

in which one of the groups $R^1$ or $R^2$ represents hydrogen or a $C_1-C_4$ alkyl group while the other is a $C_6-C_{22}$ alkyl or alkenyl group; $R^3$ represents the residue of an oligopeptide which optionally contains other MOOC—$CHR^1$—$CHR^2$—CO— groups attached to the nitrogen atom of basic amino acid side groups, and M represents hydrogen or an alkali, alkaline-earth, ammonium, mono-, di- or tri-alkanolammonium ion, are produced by partial hydrolysis of an animal or vegetable protein to a hydrolyzate having an average molecular weight of from 200 to 20,000 and reaction of the hydrolyzate with a substituted succinic acid anhydride corresponding to the following general formula

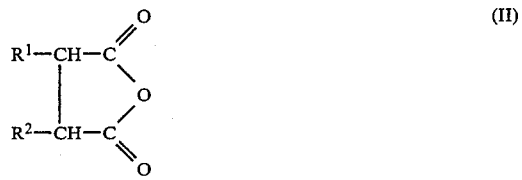

in the presence of a base at a pH value above 8. These oligopeptide derivatives are suitable for use as surfactants which are gentle to the skin.

27 Claims, No Drawings

OLIGOPEPTIDE DERIVATIVES, THEIR PRODUCTION AND THEIR USE AS SURFACTANTS GENTLE TO THE SKIN

BACKGROUND OF THE INVENTION

1. Field of the Invention

This invention relates to new oligopeptide derivatives obtainable by reaction of alkyl and alkenyl succinic acid anhydrides with protein hydrolyzates.

2. Statement of the Related Art

It is known that the compatability of surfactants and surfactant-containing preparations with the skin can be significantly improved by addition of watersoluble proteins or protein degradation products. Protein degradation products have already been incorporated in surfactants, for example products have been used which are made by acylation of protein hydrolyzates with fatty acid chlorides or by condensation of fatty acid methylesters with protein hydrolyzates. Acylated oliogopeptides of this type are known as surfactants which are gentle to the skin, and are sold under the trademarks "Lamepon" and "Maypon."

Unfortunately, the prior art fatty acid-protein hydrolyzate condensates have disadvantages in terms of practical application, for example unsatisfactory washing and foaming power, high sensitivity of the foam to water hardness and to fats. In addition, the production of fatty acid-protein hydrolyzate condensates necessitates the use either of fatty acid chlorides or, in case of the fatty acid methylesters, of high-boiling solvents (for example ethylene glycol or dimethylsulfoxide) which are undesirable in the end product.

DESCRIPTION OF THE INVENTION

It has now been found that novel protein hydrolyzates, when incorporated in surfactants, form surfactant products with improved performance properties. The novel composition of the present invention are oligopeptide derivates corresponding to the following general formula

MOOC—CHR$^1$—CHR$^2$—COHN—R$^3$  (I)

in which: one of the groups R$^1$ or R$^2$ represents hydrogen or a C$_1$–C$_4$ alkyl group while the other represents a Chd 6–C$_{22}$ alkyl or alkenyl group; R$^3$ represents the residue of an oligopeptide which has been obtained by partial hydrolysis of an animal or vegetable protein to a hydrolyzate having an average molecular weight of from 200 to 20,000 and which optionally contains other MOOC—CHR$^1$—CHR$^2$—CO— groups attached to the nitrogen atom of basic amino acid side groups in the hydrolyzate; and M represents hydrogen or an alkali, alkaline-earth, ammonium, mono-, di- or trialkanolammonium ion containing from 1 to 4 carbon atoms in the alkanol group. The group R$^3$ is the residue of an oligopeptide which is converted with the free alpha-amino group into the amide of the alkyl or alkenyl succinic acid.

The oligopeptide derivatives corresponding to formula I are obtained by reaction of a substituted succinic acid anhydride corresponding to the following formula

in which R$^1$ and R$^2$ are as defined above for formula I, with an aqueous solution of a protein hydrolyzate corresponding to the general formula R$^3$—NH$_2$, in which R$^3$ is as defined above, in the presence of a base from the group comprising alkali or alkaline-earth metal hydroxides, ammonium or a mono-, di or trialkanolamine containing from 1 to 4 carbon atoms in the alkanol group at a pH value above 8 and preferably at a pH value in the range of from 8 to 12.

The intermediate alkyl and alkenyl succinic acid anhydrides corresponding to formula II are known and may be obtained in various ways. According to U.S. Pat. No. 2,411,215, alkenyl succinic acid anhydrides may be obtained from maleic acid anhydride and monoolefins by olefin addition. Preferred monoolefins are linear alpha-olefins, for example petroleum cracking olefins or Zeigler olefins containing from 6 to 22 carbon atoms. However, it is also possible to use branched monoolefins of the type obtainable, for example, by oligomerization of propylene or butenes, for example tripropylene, tetrapropylene, diisobutene, triisobutene, and other branched monoolefins containing from 6 to 22 carbon atoms.

Another possible method of preparing alkenyl succinic acid anhydrides is to react citraconic acid anhydride or itaconic acid anhydride with a C$_6$–C$_{22}$ monoolefin in a olefin addition reaction. Starting out with citraconic acid anhydride, 1-methyl-2-alkenyl succinic acid anhydrides are obtained in this way.

The alkenyl succinic acid anhydrides may readily be converted into the corresponding alkyl succinic acid anhydrides by hydrogenation of the double bond.

The hydrolysis of proteins for the preparation of aqueous protein hydrolyzates containing oligopeptides corresponding to the formula R$^3$—NH$_2$ and having an average molecular weight of from 200 to 20,000 may be carried out by various methods known per se, for example by acidic hydrolysis, alkaline hydrolysis or by enzymatic splitting of the proteins dispersed in water. The alkaline protein hydrolysis is carried out, for example, by treating a suspension of a protein preparation with an aqueous alkali for about 1 to 20 hours at 50° to 150° C., the quantity of alkali used, for example NaOH or Ca(OH)$_2$, amounting to between about 3 and 10% by weight, based on the protein. The degree of degration, i.e., the average molecular weight of the oligopeptide obtained, may be controlled through the concentration of the alkali, the temperature and the duration of the hydrolysis reaction. The degree of degradation may be analytically determined, for example, by potentiometric titration of the content (a) of alpha-amino groups at pH 6.0–8.5 in the hydrolyzate, based on the solids content in mVal/g (i.e. millivalences per gram). On the assumption that only primary alpha-amino groups are included, the average molecular weight of the oligopeptide (MW = 1000/a) may be calculated from the value of (a). However, since the basic side groups of the basic amino acids (arginine, ornithine, lysine, hydroxylysine, histidine) present in the protein are co-titrated either completely or to a minimal extent, the value of the average molecular weight thus calculated will be slightly below the true average molecular weight.

The acidic protein hydrolysis may be carried out, for example, with aqueous hydrochloric acid or with aqueous sulfuric acid, the suspension of the protein in a 5 to 40% aqueous acid being heated under reflux to boiling temperature over a period of, for example, from 1 to 20 hours. The reaction may be considerably accelerated by heating under pressure to temperatures above 100° C.

The enzymatic degradation of proteins is preferably carried out using a protease, although it is also possible to use enzyme preparations containing, for example, protease and amylases. The enzymatic hydrolysis makes it possible, using selected proteolytic enzymes, selectively or preferentially to split bonds between certain amino acids by hydrolysis and in this way to obtain oligopeptides which preferably contain certain terminal groups. Thus, in the presence of the proteolytic enzyme trypsin, for example, the carbonamide groups of lysine and arginine are preferentially hydrolyzed, whereas the enzyme pepsin preferentially hydrolyzes the carbonamide groups of leucine, tyrosine, phenylalanine and glutamic acid.

The enzymatic hydrolysis may also be carried out in several stages, the optimal conditions (pH value and concentration) for the particular enzyme used being maintained in each stage. Processes for the enzymatic hydrolysis of proteins are known from the literature. A process for the enzymatic splitting of casein in two stages using pancreatin at pH 8 and with erepsin (mammal intestine preparation) at pH 7.6 is described in Houben-Weyl, "Methoden der Organischen Chemie," Vol. XI/2, (1958), pages 297-298. The multistage protein hydrolysis may also be carried out, for example, by initially carrying out a mild acidic or alkaline hydrolysis and then an enzymatic hydrolysis for the preparation of an oligopeptide having the desired average molecular weight range.

Protein hydrolyzates degraded to an average molecular weight of the oligopeptides of from 400 to 4000 are particularly suitable for the preparation of the oligopeptide derivatives according to the invention.

The aqueous hydrolyzates obtained by the described hydrolysis processes are further reacted either in undiluted form or, after addition of water to adjust a suitable solids content, in a concentration range of from 5 to 50% by weight. Suitable protein preparations may be of animal, vegetable or microbial origin. It is important that the protein content should be as high as possible, i.e. the content of secondary products, such as for example fats, carbohydrates, etc., should be as low as possible. Suitable proteins of the type in question are, for example, collagen from skin or connective tissue, casein, gelatin, albumin from blood, milk or eggs, keratin from hair, wool, horn, hooves and feathers, protein from leather waste, soya bean protein, almond proteins and single-cell proteins.

The substituted succinic acid anhydrides corresponding to formula II are reacted with the aqueous solution of the protein hydrolyzate in a ratio of 1 mole of the oligopeptide (calculated from the content of free alpha-amino groups) to 0.6-6 moles of the substituted succinic acid anhydride and preferably in a ratio of 1 mole of the oligopeptide to 1-3 moles of the substituted succinic acid anhydride. By addition of dilute alkali, for example dilute alkali metal hydroxide such as sodium hydroxide, the pH of the reaction mixture is kept at a value above 8 and preferably at pH 9 to pH 11. The reaction temperature is best in the range of from 50° to 80° C. Under these conditions, no more alkyl or alkenyl succinic acid anhydride can be detected after 2 to 6 hours. The alkyl succinic acid anhydride may be added in either free from or in the form of a solution in a low-boiling, water-miscible aprotic solvent, such as, for example acetone, butanone, tetrahydrofuran, 1,2-dimethoxy ethane or acetonitrile.

Hydrolysis of the alkyl or alkenyl succinic acid anhydride to the alkyl or alkenyl succinic acid occurs as a secondary reaction. By neutralization of the reaction mixture, for example with dilute mineral acid, such as hydrochloric acid or sulfuric acid, to pH 5-7 and extraction with a water-immiscible solvent, the reaction mixture may be freed from water-insoluble secondary products which are not attached to the oligopeptide, i.e. mainly alkyl or alkenyl succinic acid. A suitable solvent for this extraction is, for example, methyl tert.-butylether (MTBE). Unreacted protein hydrolyzate, which is also present to a slight extent in the reaction product, may remain in the product because it does not affect the performance properties and actually improves the cosmetic-dermatological properties of the oligopeptide derivatives.

Oligopeptide derivatives of formula I according to the invention, in which one of the groups $R^1$ or $R^2$ represents hydrogen and the other is a linear $C_8$-$C_{18}$ alkyl or alkenyl group, show particularly favorable performance properties. $R^3$ is, preferably, the residue of an oligopeptide which has been obtained by partial hydrolysis of an animal protein, preferably a gelatin or a leather protein, to an average molecular weight of the oligopeptides of from 400 to 4000.

The oligopeptide derivatives according to the invention are new, high foaming surfactants which are particularly gentle to the skin and mucous membrane. They are suitable for use as surfactants in liquid washing and cleaning preparations, more especially in cosmetic washing preparations for the skin and hair. However, the new oligopeptide derivatives may also be used with advantage in manual dishwashing preparations or in detergents and cleaning preparations which, in use, come into contact with the skin. The oligopeptide derivatives according to the invention are readily miscible and compatible with any known anionic, nonionic, amphoteric and zwitterionic surfactants. They have the advantage that, in admixture with particularly high foaming anionic surfactants, more especially alkyl sulfates and alkylether sulfates, their foaming power is not adversely affected. Accordingly, they are eminently suitable for use as co-surfactants for improving the dermatological properties and for improving the trichocosmetic effects of cosmetic surfactant preparations for cleaning and caring for the skin and the hair; for use, for example, in shampoos, foam baths, shower baths, liquid soaps, washing lotions.

Preparations of the type in question preferably contain from 3 to 30% by weight of alkyl (polyglycolether) sulfates corresponding to the following general formula $$R^4\text{—O—}(C_2H_4O)_n\text{—}SO_3M^1 \qquad (III)$$

in which $R^4$ is a preferably linear $C_{10}$-$C_{16}$ alkyl group, $n=0$ or an integer of from 1 to 12 and $M^1$ is an alkali, ammonium, mono-, di- or trialkanolammonium ion containing from 1 to 4 carbon atoms in the alkanol group or, in the case of the alkyl polyglycolether sulfates (n=1-12), may even be a magnesium ion. The oligopeptide derivatives are present in the cosmetic surfactant preparations preferably in a ratio by weight of from 1:20 to 1:1 to the alkyl sulfates and/or alkylether sulfates.

The following Examples are intended to illustrate the invention without limiting it in any way:

EXAMPLES

1. Preparation of protein hydrolyzates

Partial hydrolysis of gelatin 1.1 600 g of gelatin were taken up in 900 ml of water and, after the addition of 24 g of sodium hydroxide, the solution was heated for 16 hours to 130° C. in a stirrer-equipped autoclave. The solution was then diluted to a solids content of approximately 20% by weight by addition of 1500 ml of water.

The content (a) of alpha-amino groups in the hydrolyzate, based on the solids content in mVal/g, was determined by potentiometric titration. The average molecular weight of the oligopeptide was calculated therefrom in accordance with the equation $MW = 1000/a$. The average molecular weight (MW) was 1060.

1.2 100 g of gelatin were take up in 150 ml of water and 4 g of calcium hydroxide added to the resulting solution which was then heated for 16 hours to 130° C. in a stirrer-equipped autoclave. The solution was then diluted to a solids content of approximate 20% by weight by addition of 250 ml of water. The protein hydrolyzate had an average molecular weight of approximate 1690.

Partial hydrolysis of leather protein 1.3 400 g of leather protein (from leather waste) were suspended in 900 ml of water and, after the addition of 16 g of sodium hydroxide, the resulting suspension was heated for 16 hours to 130° C. in a stirrer-equipped autoclave. After separation by filtration from a little undissolved residue, the product was diluted to a solids content of approximately 20% by weight by addition of 700 ml of water. The product has an average molecular weight of 1030.

1.4 100 g of leather protein (from leather waste) were suspended in 150 ml of water and, after the addition of 4 g of calcium hydroxide, the resulting suspension was heated for 16 hours to 130° C. in a stirrer-equipped autoclave. After separation of a little undissolved residue, the product was adjusted to a solids content of approximately 20% by weight by addition of 250 ml of water. The average molecular weight of the hydrolyzate was 1970.

2. Preparation of reaction products of alkenylsuccinic acid anhydride and protein hydrolyzate 2.1 10.6 g (0.04 mole) of n-dodecenylsuccinic acid anhydride were added with stirring at 70° C. to 100 g of a protein hydrolyzate solution prepared according to 1.1. The pH value of the reaction mixture was kept at 11 by addition of dilute sodium hydroxide. After a reaction time of 4 hours, the mixture was cooled to 20° C. and adjusted with dilute hydrochloride acid to a pH value of 7.

2.5 g of water-insoluble secondary products (mainly unreacted alkenylsuccinic acid) were removed from the reaction mixture by extraction with methyl tert.-butylether (MTBE). Traces of MTBE were removed from the aqueous phase by heating to 40° C. in a water jet vacuum.

Analysis of the anhydrous solid revealed 9.7% by weight of N and 2.7% by weight of Cl.

2.2 100 g of the protein hydrolyzate solution prepared according to 1.1 were reacted as in 2.1 with 22.6 g (0.06 mole) of a mixture of n-hexadecenyl and n-octadecenyl succinic acid anhydride (ratio by weight 55:45) at a pH-value of 10. Approximately 4.7 g of water-insoluble secondary products were separated off from the reaction mixture by extraction with MTBE.

Analysis of the dried solid revealed 7.9% by weight N, 2.4% by weight Cl and 2.0% by weight $H_2O$.

2.3 100 g of the protein hydrolyzate solution prepared according to 1.3 were reacted as in 2.1 with 21.3 g (0.08 mole) of an n-dodecenyl succinic acid anhydride. Approximately 7 g of water-insoluble secondary products were separated off from the reaction mixture by extraction with MTBE.

Analysis of the dried solid revealed 10.1% by weight N and 2.8% by weight Cl.

2.4 100 g of the protein hydrolyzate solution prepared according to 1.3 were reacted as in 2.1 with 31.9 g (0.12 mole) of an n-dodecenyl succinic acid anhydride. 12.8 g of water-insoluble secondary products were separated off from the reaction mixture by extraction with MTBE.

Analysis of the dried solid revealed 11.1% by weight N.

2.5 100 g of the protein hydrolyzate solution prepared according to 1.1 were reacted as in 2.1 with 22.6 g (0.10 mole) of an n-dodecenyl succinic acid anhydride at 50° C./pH 10.5. 16.8 g of water-insoluble secondary products were separated off from the reaction mixture by extraction with MTBE.

2.6 100 g of the protein hydrolyzate solution prepared according to 1.2 were reacted as in 2.1 with 16 g (0.06 mole) of an n-dodecenyl succinic acid anhydride. Neutralization was carried out with dilute sulfuric acid. The mixture was then filtered off from small quantities of undissolved fractions. 6.4 g of water-insoluble secondary products were separated off from the mixture by extraction with MTBE. Analysis of the dried product revealed 13.9% by weight N.

2.7 100 g of the protein hydrolyzate solution prepared according to 1.4 were reacted as in 2.1 with 16 g (0.06 mole) of n-dodecenyl succinic acid anhydride. 4.2 g of water-insoluble secondary products were separated off from the mixture by extraction with MTBE.

Analysis of the dried reaction product revealed 12.6% by weight N.

3. Testing of the foaming properties

Foaming power was tested in accordance with DIN 53902-T01. In this test, foam is produced by beating 200 ml of a solution of the surfactant in a 1 liter cylinder for 30 seconds with a perforated plate fixed to a shaft at a rate of 1 beat per second. The foam volume of the sample solution is measured 30 seconds after the end of beating.

Table I shows the foam volume at 40° C. for product concentrations of 0.5 g/l, 1.0 g/l, 2.0 g/l and 3 g/l and a water hardness of 0° d, 10° d and 20° d.

Table II shows the foam value for a mixture of fatty alcohol ($C_{12}$–$C_{14}$) poly(2EO)glycolether sulfate, Na salt (FES), and the oligopeptide derivate in a ratio by weight of 7:3 at 40° C. and at graduated overall concentrations of 0.5 g/l, 1.0 g/l, 2.0 g/l and 3 g/l for a water hardness of 10° d.H (1° d corresponds to 10 mg/l of CaO or 0.357 mval/l alkaline-earth ions).

TABLE I

| Oligopeptide Derivative | Concentration | Water Hardness | | |
|---|---|---|---|---|
| | | 0° d | 10° d | 20° d |
| Example 2.3 | 0.5 g/l | 100 ml | 130 ml | 160 ml |
| | 1.0 g/l | 130 ml | 230 ml | 250 ml |
| | 2.0 g/l | 250 ml | 350 ml | 390 ml |
| | 3.0 g/l | 500 ml | 520 ml | 500 ml |
| Example 2.7 | 0.5 g/l | 250 ml | 70 ml | 50 ml |
| | 1.0 g/l | 250 ml | 110 ml | 160 ml |
| | 2.0 g/l | 390 ml | 190 ml | 210 ml |
| | 3.0 g/l | 560 ml | 240 ml | 240 ml |

TABLE II

| Surfactant | Concentration | Foam volume at 10° d |
|---|---|---|
| 70% by weight FES 30% by weight Example 2.3 | 0.5 g/l | 500 ml |
| | 1.0 g/l | 670 ml |
| | 2.0 g/l | 790 ml |
| | 3.0 g/l | 900 ml |
| FES | 1.0 g/l | 740 ml |
| | 3.0 g/l | 910 ml |

As can be seen from the above data the oligopeptide derivatives of the invention have excellent foaming properties and as pointed out above, when they are used in admixture with other high foaming anionic surfactants, the foaming power is not adversely affected.

We claim:

1. Oligopeptide derivates corresponding to the general formula $$\text{MOOC—CHR}^1\text{—CHR}^2\text{—COHN—R}^3 \qquad (I)$$

in which one of the groups $R^1$ or $R^2$ represents hydrogen or a $C_1$-$C_4$ alkyl group while the other represents at least one $C_6$-$C_{22}$ alkyl or alkenyl group; $R^3$ represents the residue of an oligopeptide which has been obtained by partial hydrolysis of an animal or vegetable protein to a hydrolyzate having an average molecular weight of from 200 to 20,000 and M represents hydrogen or an alkali, alkaline-earth, ammonium, mono-, di- or trialkanolammonium ion containing from 1 to 4 carbon atoms in the alkanol group.

2. Oligopeptide derivatives as claimed in claim 1, characterized in that one of the groups $R^1$ or $R^2$ represents hydrogen while the other is a $C_8$-$C_{18}$ alkyl or alkenyl group.

3. An oligopeptide derivative as claimed in claim 1 or 2, characterized in that the oligopeptide has been obtained by partial hydrolysis of an animal protein to a hydrolyzate having an average molecular weight of from 400 to 4000.

4. The oligopeptide derivative of claim 3 wherein the protein is a leather protein.

5. The oligopeptide derivative of claim 3 wherein the protein is gelatin.

6. An oligopeptide derivative as claimed in claim 1 or 2, which contains MOOC—CHR$^1$—CHR$^2$—CO— groups attached to the nitrogen atom of basic amino side groups in said hydrolyzate.

7. A process for the preparation of oligopeptide derivatives corresponding to the general formula $$\text{MOOC—CHR}^1\text{—CHR}^2\text{—COHN—R}^3 \qquad (I)$$

in which one of the groups $R^1$ or $R^2$ represents hydrogen or a $C_1$-$C_4$ alkyl group while the other represents at least one $C_6$-$C_{22}$ alkyl or alkenyl group and $R^3$ represents the residue of an oligopeptide which has been obtained by partial hydrolysis of an animal or vegetable protein to a hydrolyzate having an average molecular weight of from 200 to 20,000 and M represents an alkali, alkaline-earth, ammonium, mono-, di- or trialkanolammonium cation contining from 1 to 4 carbon atoms in the alkanol group, characterized in that a substituted succinic acid anhydride corresponding to the general formula

in which $R^1$ and $R^2$ are as defined above, is reacted at a pH value of above 8 with an aqueous solution of a protein hydrolyzate corresponding to the general formula $H_2N$—$R^3$ where $R^3$ is as defined above, in the presence of a base from the group comprising alkali or alkaline-earth metal hydroxides, ammonium or a mono-, di- or trialkanolamine containing from 1 to 4 carbon atoms in the alkanol group.

8. The process of claim 7 wherein MOOC—CHR$^1$—CHR$^2$—CO— groups are attached to the nitrogen atom of basic amino sidegroups in said hydrolyzate.

9. A process as claimed in claims 7 or 8 wherein water-insoluble secondary products which are not attached to the oligopeptide residue are removed from the reaction mixture by extraction with an organic water-immiscible solvent at a pH value of 5 to 7.

10. An aqueous cosmetic surfactant composition having high foaming power and which is gentle to the skin comprising water and surfactant effective amount of at least one oligopeptide derivate corresponding to the general formula $$\text{MOOC—CHR}^1\text{—CHR}^2\text{—COHN—R}^3 \qquad (I)$$

in which one of the groups $R^1$ or $R^2$ represents hydrogen or a $C_1$-$C_4$ alkyl group while the other represents at least one $C_6$-$C_{22}$ alkyl or alkenyl group; $R^3$ represents the residue of an oligopeptide which has been obtained by partial hydrolysis of an animal or vegetable protein to a hydrolyzate having an average molecular weight of from 200 to 20,000 and M represents hydrogen or an alkali, alkaline-earth, ammonium, mono-, di- or trialkanolammonium ion containing from 1 to 4 carbon atoms in the alkanol group.

11. The surfactant composition of claim 10 containing from 3 to 30% by weight of an alkyl (polyglycolether) sulfate of the formula $$R^4\text{—O—}(C_2H_4O)_n\text{—SO}_3M^1 \qquad (III)$$

in which $R^4$ is a linear $C_{10}$-$C_{16}$ alkyl group, n is 0 or an integer of from 1 to 12 and $M^1$ is an alkali, ammonium, mono-, di- or trialkanolammonium ion containing from 1 to 4 carbon atoms in the alkanol group.

12. The surfactant composition of claim 11 where n is 0 and $M^1$ is magnesium.

13. The surfactant composition of claim 11 or 12 wherein the weight ratio of said oligopeptide derivative to the alkyl(polyglycolether)sulfate is from 1:20 to 1:1.

14. An oligopeptide derivative as claimed in claim 3 which contains MOOC—CHR$^1$—CHR$^2$—CO— groups attached to the nitrogen atom of basic amino side groups in said hydrolyzate.

15. The oligopeptide derivative of claim 3 wherein said $C_6$-$C_{22}$ alkyl or alkenyl group is at least one of n-dodecenyl, n-hexadecenyl, or n-octadecenyl.

16. The oligopeptide of claim 1 or 2 wherein said (alkyl or alkenyl group) has 8 to 18 carbon atoms.

17. The oligopeptide derivative of claim 15 wherein said animal protein is a leather protein or gelatin.

18. An oligopeptide derivative as claimed in claim 17 which contains MOOC—CHR$^1$—CHR$^2$—CO— groups attached to the nitrogen atom of basic amino side groups in said hydrolyzate.

19. The process of claim 7 wherein said protein is a leather protein or gelatin and said (alkyl or alkenyl group) has 8 to 18 carbon atoms.

20. The process of claim 19 wherein said $C_6$-$C_{22}$ alkyl or alkenyl group is at least one of n-dodecenyl, n-hexadecenyl, or n-octadecanyl.

21. The process of claim 20 wherein MOOC—CHR$^1$—CHR$^2$—CO— groups are attached to the nitrogen atom of basic amino side groups in said hydrolyzate.

22. A process as claimed in claim 21 wherein water-insoluble secondary products which are not attached to the oligopeptide residue are removed from the reaction mixture by extraction with an organic water-immiscible solvent at a pH value of 5 to 7.

23. The surfactant composition of claim 10 wherein said $C_6$-$C_{22}$ alkyl or alkenyl group is at least one of n-dodecenyl, n-hexadecenyl, or n-octadecenyl.

24. An oligopeptide derivative as claimed in claim 10 which contains MOOC—CHR$^1$—CHR$^2$—CO— groups attached to the nitrogen atom of basic amino side groups in said hydrolyzate.

25. An oligopeptide derivative as claimed in claim 23 which contains MOOC—CHR$^1$—CHR$^2$—CO— groups attached to the nitrogen atom of basic amino side groups in said hydrolyzate.

26. The surfactant composition of claim 10 wherein said protein is a leather protein or gelatin.

27. The surfactant composition of claim 25 wherein said protein is a leather protein or gelatin.

* * * * *